United States Patent
Mann

(10) Patent No.: US 9,603,890 B2
(45) Date of Patent: *Mar. 28, 2017

(54) METHODS FOR INCREASING THE SELECTIVE EFFICACY OF GENE THERAPY USING CAR PEPTIDE AND HEPARAN-SULFATE MEDIATED MACROPINOCYTOSIS

(71) Applicant: Vascular Biosciences, San Diego, CA (US)

(72) Inventor: David Mann, San Diego, CA (US)

(73) Assignee: Vascular Biosciences, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/649,455

(22) PCT Filed: Dec. 3, 2013

(86) PCT No.: PCT/US2013/072768
§ 371 (c)(1),
(2) Date: Jun. 3, 2015

(87) PCT Pub. No.: WO2014/089017
PCT Pub. Date: Jun. 12, 2014

(65) Prior Publication Data
US 2016/0022759 A1 Jan. 28, 2016

Related U.S. Application Data

(60) Provisional application No. 61/732,859, filed on Dec. 3, 2012.

(51) Int. Cl.
*A61K 38/08* (2006.01)
*G01N 33/68* (2006.01)
*A61K 45/06* (2006.01)
*C12Q 1/34* (2006.01)

(52) U.S. Cl.
CPC .............. *A61K 38/08* (2013.01); *A61K 45/06* (2013.01); *C12Q 1/34* (2013.01); *G01N 33/6893* (2013.01); *G01N 2333/926* (2013.01); *G01N 2800/12* (2013.01); *G01N 2800/321* (2013.01)

(58) Field of Classification Search
None
See application file for complete search history.

(56) References Cited

U.S. PATENT DOCUMENTS

| 5,795,875 | A | 8/1998 | Holme et al. | |
|---|---|---|---|---|
| 7,781,416 | B2 * | 8/2010 | Casu | A61K 31/727 514/54 |
| 8,741,861 | B2 * | 6/2014 | Mann | C12Q 1/6883 514/15.7 |
| 2010/0323991 | A1 | 12/2010 | Bar-Or | |

| 2011/0033876 | A1 | 2/2011 | Mouthon et al. |
| 2011/0280798 | A1 | 11/2011 | Chang et al. |
| 2011/0294869 | A1 | 12/2011 | Petersen |
| 2012/0034164 | A1 | 2/2012 | Ruoslahti et al. |

FOREIGN PATENT DOCUMENTS

WO   WO 2011106788 A2 *  9/2011  ............... C07K 7/06

OTHER PUBLICATIONS

Sampaio, Lucia O. et al, "Heparins and heparin sulfates. Structure, distribution and protein interactions." in Insights into carbohydrate structure and function (2006) ISBN 81-7895-243-2, Hugo Verli, ed.*
Yampolsky, Lev Y. and Stoltzfus, Arlin, "The exchangeability of amino acids in proteins." Genetics (2005) 170 p. 1459-1472.*
Reilly, John P. et al, "The darc side of glycobiology in acute lung injury." Chest (2012) 141(5) p. 1132-1133.*
The Komen foundation press report, 2010, available at http://ww5.komen.org/Breast-Cancer-News/BRCA1/2-Mutations-Linked-with-Better-Outcome-in-Triple-negative-Breast-Cancer.html.*
Urakami, Takeo et al, "Peptide directed highly selective targeting of pulmonary arterial hypertension." Amer. J. Pathol. (2011) 178(6) p. 2489-2495.*
Schenauer, Matthew R. et al, "Heparan sulfate separation, sequencing, and isomeric differentiation: ion mobility spectrometry reveals specific iduronic and glucoronic acid containing hexasaccharides." Anal. Chem. (2009) 81 p. 10179-10185.*
GDS4579, available online at http://www.ncbi.nlm.nih.gov/geo/tools/profileGraph.cgi?ID=GDS4579:1368407_at, downloaded Apr. 4, 2016.*
GDS3580 available online at http://www.ncbi.nlm.nih.gov/geo/tools/profileGraph.cgi?ID=GDS3580:203284_s_at, downloaded Apr. 4, 2016.*
GDS3463 available online at http://www.ncbi.nlm.nih.gov/geo/tools/profileGraph.cgi?ID=GDS3463:232276_at, downloaded Apr. 4, 2016.*
Hassoun, Paul M. et al, "Inflammation, growth factors, and pulmonary vascular remodeling." J. Am. Col. Cardiology (2009) 54(1) suppl S, p. S10-S19.*
Urakami et al., "Peptide-directed highly selective targeting of Pulmonary Arterial Hypertension." American Journal of Pathology (2011) 178(6): 2489-2495.

* cited by examiner

*Primary Examiner* — Fred Reynolds
(74) *Attorney, Agent, or Firm* — Lewis Kohn & Walker LLP; David M. Kohn; Kari Moyer-Henry

(57) ABSTRACT

Disclosed are compositions and methods for triggering disease selective macropinocytosis. The compositions can serve as a marker of disease activity and as a trigger of enhanced macropinocytosis in tissues undergoing disease remodeling such as wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The compositions can also serve as a receptor for disease selective cell penetrating peptides in the cells and extracellular matrix of diseased tissues.

2 Claims, 3 Drawing Sheets

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Cys Ala Arg Ser Lys Asn Lys Asp Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthesized

<400> SEQUENCE: 2

Cys Ala Arg Ser Lys Asn Lys
1               5
```

METHODS FOR INCREASING THE SELECTIVE EFFICACY OF GENE THERAPY USING CAR PEPTIDE AND HEPARAN-SULFATE MEDIATED MACROPINOCYTOSIS

RELATED APPLICATIONS

This application is a United States National Stage Application claiming priority under 35 U.S.C. 371 from International Patent Application No. PCT/US13/72768 filed on Dec. 3, 2013, which claims priority from U.S. Provisional Application No. 61/732,859, filed on Dec. 3, 2012, the contents of which are hereby incorporated by reference herein.

FIELD OF THE INVENTION

The present invention relates generally to the field of molecular medicine, and specifically to cell and tissue targeting peptides.

BACKGROUND OF THE INVENTION

Cell penetrating peptides were first discovered through efforts to describe how HIV (Human Immunodefficiency Virus) enters cells (Frankel 1988, Green 1988). This led to the discovery of the TAT (Trans-Activator of Transcription) protein encoded as the TAT gene within the HIV-1 virus as the protein responsible for cell penetration and the identification of the protein transduction domain, YGRKKRRQRRR, as the first cell penetrating peptide capable of entering the cell membrane (Lindsay 2002, Wadia 2003, Snyder 2004). Since the discovery of the TAT transduction domain, other cell penetrating peptides have been discovered (Saalik 2004).

Cell penetrating peptides have proven to be a useful tool for the delivery of proteins, small molecule drugs, antibodies, and other therapeutic compounds into cells and are currently being tested in clinical trials (Johnson 2011). Cell penetrating homing peptides have proven to be even more useful in that they can penetrate cells selectively by tissue type or areas of disease (Ruoslahti 2000, Kaplan 2005, Nishimura 2008).

While most cell penetrating peptides have been conjugated or electrostatically bound to the desired therapeutic payload (Niesner 2002, Brooks 2005), recent experiments have described the ability of a disease homing, cell-penetrating peptide CARSKNKDC (CAR) to enhance the ability of co-administered vasodilators (fasudil, Y-27632, imatinib, and sildenafil) to selectively lower pulmonary pressure in animal models of pulmonary arterial hypertension (PAH) (PCT/US11/26535) and additional experiments by Jirvinen and Ruoslahti have described CAR's ability by itself to promote wound healing (U.S. patent application Ser. No. 13/406,699).

However, the mechanism by which CAR enables the selective uptake of co-administered drugs and promotes wound healing has not been previously described. Furthermore the receptor to which CAR homes to is yet to be identified.

There is a need to understand the mechanism by which CAR works, and the receptor to which it binds. The benefits of identifying the mechanism are numerous, including developing novel diagnostic preparations used to aid in the development of new treatments for a variety of diseases. Identification of the receptor and understanding the related mechanism of action will lead to novel disease applications of cell penetrating peptides.

SUMMARY OF THE INVENTION

Heparan sulfate is a sulfated polysaccharide that is found on the cell surface and extracellular matrix of all human cells. It interacts with a variety of proteins and is thus involved in numerous biological processes such as growth and development. Heparan sulfate's function critically depends on the number and the position of sulfate groups, which modulate the binding sites for proteins such as growth factors, cytokines, receptors, enzymes, and inhibitors. However, little is known about their roles both in vitro and in vivo.

Disclosed herein is a heparan sulfate moiety, 2-O-sulfo-α-L-iduronic acid-2-deoxy-2-acetamido-α-D-glucopyranosyl (IdoA2S-GlcNS), capable of triggering disease selective macropinocytosis. The moiety disclosed herein can serve as a marker of disease activity and as a trigger of enhanced macropinocytosis in tissues undergoing disease remodeling such as wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The moiety disclosed herein can also serve as a receptor for disease selective cell penetrating peptides in the cells and extracellular matrix of diseased tissues.

Also disclosed herein is a sulfotransferase enzyme, Heparan sulfate 2-O-sulfotransferase-1 (HS2ST1), involved in the synthesis of IdoA2S-GlcNS. The sulfotransferase enzyme disclosed herein can serve as a marker of diseases such as wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The sulfotransferase enzyme disclosed herein can also serve as a marker for the need for enhanced macropinocytosis in the tissues expressing elevated levels of HS2ST1. Methods of treating diseases characterized by elevated HS2ST1 are also disclosed herein.

Alterations in heparan sulfation may be associated with pathologic conditions such as cancer. Heparan sulfate 6-O-sulfotransferases (HS6STs) catalyze the transfer of sulfate groups to the carbon 6 position in heparan sulfate. Three isoforms of these enzymes have been discovered in humans. Disclosed herein is a Heparan sulfate 6-O-sulfotransferase-3, (HS6ST3), which can serve as a marker of diseases such as wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The sulfotransferase enzyme disclosed herein can also serve as a marker for the need for enhanced macropinocytosis in the tissues expressing elevated levels of HS6ST3. Methods of treating diseases characterized by elevated HS6ST3 are also disclosed herein.

Also disclosed herein is a heparan sulfate degrading enzyme, heparanase (HPSE), involved in the degradation and cleavage of heparan sulfate moieties. The enzyme disclosed herein can serve as a marker of diseases such as wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The enzyme disclosed herein can also serve as a marker for the need for enhanced macropinocytosis in the tissues expressing elevated levels of HPSE. Methods of treating diseases characterized by elevated HPSE are also disclosed herein.

Also disclosed herein are methods for improving the selective efficacy of gene therapy. Disclosed are methods wherein the selective efficacy of gene therapy is increased in a localized manner for wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome. The methods of gene therapy disease selective enhancement disclosed herein can involve co-administration with the gene therapy and can be orally available.

Also disclosed herein are methods of treating diseases characterized by decreased macropinocytosis by administering a disease selective macropinocytosis promoter. The disease characterized by decreased macropinocytosis can be wound healing, cancer, PAH, inflammation, diabetes, Crohn's disease, ulcerative colitis, ankylosing spondylitis, diseases of the endometrium, psoriasis, irritable bowel syndrome, arthritis, fibrotic disorders, interstitial cystitis, autoimmune diseases, asthma, acute lung injury, and adult respiratory distress syndrome and the disease selective macropinocytosis promoter can be a cell penetrating peptide. The disease selective macropinocytosis promoters disclosed herein can involve co-administration with the gene therapy and can be orally available.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed invention, and together with the description, serve to explain the principles of the disclosed methods.

Figure 1:
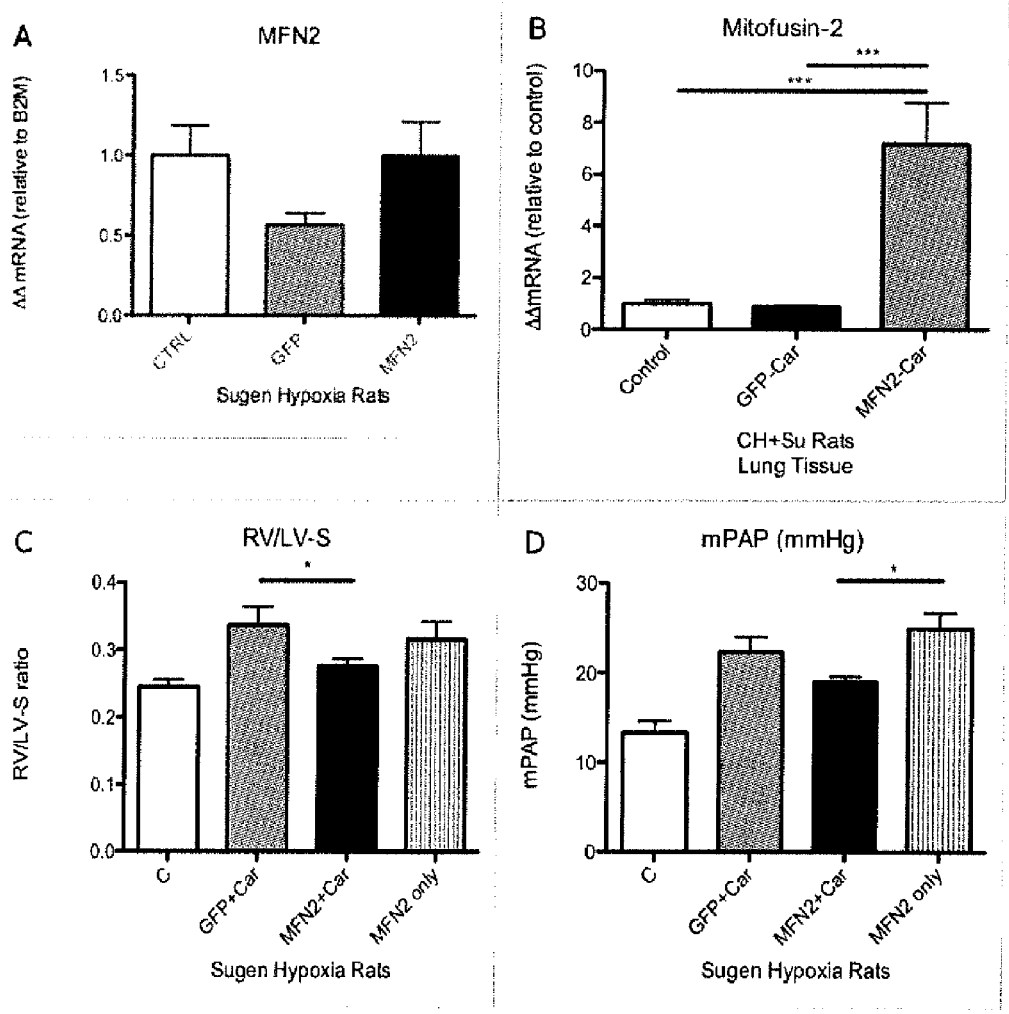
FIG. 1 shows the effects of co-administered CAR peptide on gene therapy. CAR peptide was able to exert its disease-selective adjuvant properties by allowing enhanced viral delivery and uptake of gene product (MFN2) in an animal model of severe occlusive PAH in rats. (A) Figure showing the effect of MFN2 GTx administered alone when compared to control and diseased animal not given MFN2 Gtx. Statistical significance was examined using ANOVA (see Supplement for further statistical information). (B) Change in mitofusion-2 mRNA levels relative to control. The results indicate that MFN2 GTx is significantly enhanced in the presence of CAR peptide. (C) The RV/LV-S ratio returned to near-normal (non-diseased/control) levels following co-administration of CAR with MFN2 GTx. (D) mPAP (mmHg) levels in Sugen hypoxia rats. CAR+MFN2 GTx reduced pressure levels more than when MFN2 GTx was administered alone.

Adenoviruses were used as viral delivery vectors to incorporate cDNA inserts of MFN2 into rats with severe occlusive pulmonary hypertension induced by Sugen injection followed by hypoxia (FIG. 1). The results indicated that when administered alone, MFN2 gene therapy brought MFN2 mRNA gene expression levels to within normal range (FIG. 1A). In contrast to the administration of MFN2 GTx alone (MFN2 only), when CAR was co-administered with MFN2 GTx, (MFN2-CAR), MFN2 mRNA expression levels were significantly elevated, greater than 7× above both control levels and MFN2 Gtx levels of MFN2 expression (P=0.001) (FIG. 1B). Additionally, the ratio of right ventricle to left ventricle+septum weight ratio (RV/LV-S ratio) returned to almost normal when CAR was co-administered with the MFN2 GTx (FIG. 1C). Finally, Sugen hypoxia rats treated with MFN2 GTx and CAR peptide displayed pulmonary arterial pressure (mPAP) reductions that were significantly larger (P<0.5) than PAH rats treated only with MFN2 adenovirus gene therapy (FIG. 1D).

Figure 2:
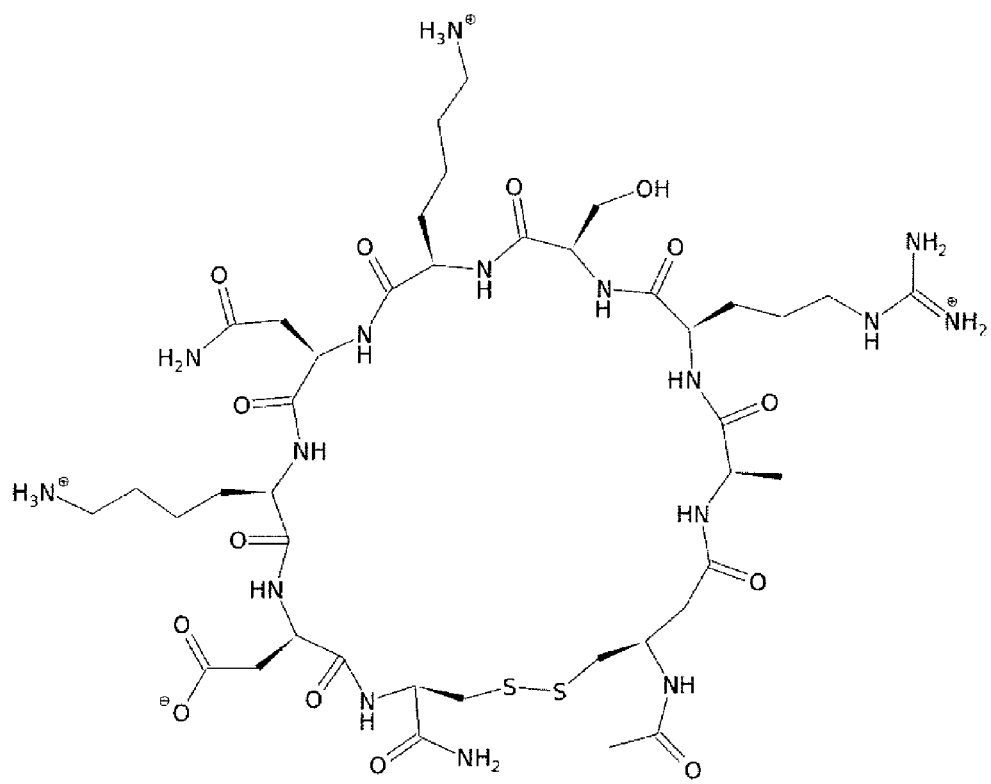

FIG. 2 shows the chemical structure of SEQ ID NO:1, CARSKNKDC (CAR).

Figure 3:
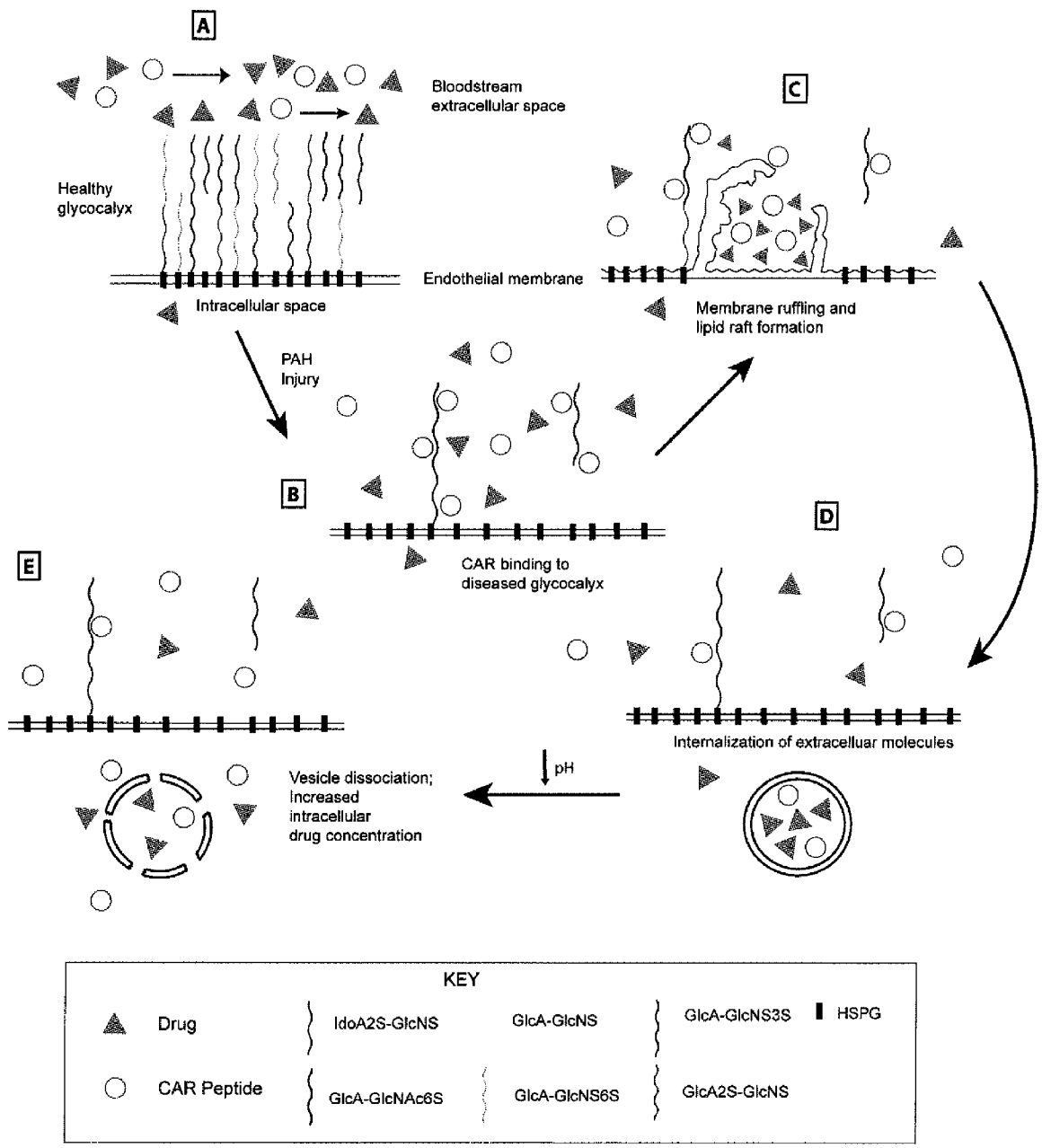

FIG. 3 shows CAR peptide binding and internalization mechanism of action. FIG. 3a shows healthy glycocalyx located on endothelial cell surface facing the bloodstream. FIG. 3b shows the result of PAH injury. FIG. 3c shows the initiation of heparan sulfate-mediated macropinocytosis. FIG. 3d shows vesicle formation and CAR internalization by cells. FIG. 3e shows release of CAR into diseased cells.

DETAILED DESCRIPTION OF THE INVENTION

The disclosed methods and compositions can be understood more readily by reference to the following detailed description of particular embodiments and the Examples included therein and to the Figures and their previous and following description.

Before the present compounds, compositions, articles, devices, and/or methods are disclosed and described, it is to be understood that they are not limited to specific synthetic methods of specific recombinant biotechnology methods unless otherwise specified, or to particular reagents unless otherwise specified, as such may, of course, vary. It is also to be understood that the terminology used herein is for the purposes of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or much such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

The term "bioactive agent" refers to a substance which is used in connection with an application that is therapeutic or diagnostic in nature, such as in methods for diagnosing the presence or absence of a disease in a patient and/or in methods for treating a disease in a patient. As to compatible bioactive agents, those skilled in the art will appreciate that any therapeutic or diagnostic agent may be incorporated in the stabilized dispersions of the present invention. For example, the bioactive agent may be selected from the group consisting of antiallergics, bronchodilators, vasodilators, antihypertensive agents, bronchoconstrictors, pulmonary lung surfactants, analgesics, antibiotics, leukotriene inhibitors or antagonists, anticholinergics, mast cell inhibitors, antihistamines, anti-inflammatories, anti-neoplastics, anesthetics, anti-tuberculars, imaging agents, cardiovascular agents, enzymes, steroids, genetic material, viral vectors, antisense agents, small molecule drugs, proteins, peptides and combinations thereof. Particularly preferred bioactive agents comprise compounds which are to be administered systemically (i.e. to the systemic circulation of a patient) such as small molecule drugs, imaging agents, peptides, proteins or polynucleotides. As will be disclosed in more detail below, the bioactive agent may be incorporated, blended in, coated on or otherwise associated with the targeting peptide disclosed herein. Particularly preferred bioactive agents for use in accordance with the invention include anti-allergics, peptides and proteins, bronchodilators, anti-inflammatory agents and anti-cancer compounds for use in the treatment of disorders involving diseased tissue reflecting altered heparan sulfate variants specific to said disease. Yet another associated advantage of the present invention is the effective delivery of bioactive agents administered or combined with a targeting peptide. As used herein, the term "dendrimer" shall mean repeatedly branched and roughly spherical molecules. A dendrimer is typically symmetric around a core and usually adopts a spherical three-dimensional morphology. Dendrimers generally contain three major portions: a core, an inner shell and an outer shell. Dendrimers can be synthesized to have different and varying functionality in each of the major portions in order to control such variables as solubility, thermal stability and attachment of compounds suitable for particular applications.

"Optional" or "optionally" means that subsequently described event or circumstance may or may not occur, and that the description includes instances where said event or circumstance occurs and instances where it does not.

As used herein, the phrase "other compounds and compositions" is used broadly such that "compounds" and "compositions" may mean a nanoparticle, a nanoworm, an iron oxide nanoworm, an iron oxide nanoparticle, an albumin nanoparticle, a liposome, a micelle, a phospholipid, a polymer, a microparticle, a fluorocarbon microbubble, a therapeutic agent, a therapeutic protein, a therapeutic compound, a therapeutic composition, a chemotherapeutic agent, a cancer chemotherapeutic agent, a toxin, a cytotoxic agent, Abraxane, paclitaxel, taxol, imatinib, an anti-angiogenic agent, a pro-angiogenic agent, an anti-inflammatory agent, an anti-arthritic agent, a TGF-B inhibitor, decorin, a systemic vasodilator, an anti-coagulant, tissue factor pathway inhibitor (TFPI), site-inactivated factor VIIa, a B-2 agonist, salmeterol, formoterol, N-Acetylcysteine (NAC), Superoxide Dismutase (SOD), a superoxide dismutase mimetic, EUK-8, an endothelin (ET-1) receptor antagonist, a prostacyclin derivative, a phosphodiesterase type 5 inhibitor, Ketoconazole, an antibody, a small interfering RNA (siRNA), a microRNA (miRNA), a polypeptide, a nucleic acid molecule, a small molecule, a carrier, a vehicle, a virus, a phage, a viral particle, a phage particle, a viral capsid, a phage capsid, a virus-like particle, a liposome, a micelle, a bead, a nanoparticle, a microparticle, a detectable agent, a contrast agent, an imaging agent, a label, a labeling agent, a fluorophore, fluorescein, rhodamine, FAM, a radionuclide, indium-111, technetium-99, carbon-11, or carbon-13 and the like.

As used herein, the term "peptide" is used broadly to mean peptides, proteins, fragments of proteins and the like. Protein variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct.

The mutations must not place the sequence out of reading frame and preferably will not create complementary regions that could produce secondary mRNA structure. Substitutional variants are those in which at least one residue has been removed and a different residue inserted in its place.

The phrase "substantially identical" means that a relevant sequence is at least 70%, 75%, 80%, 85%, 90%, 92%, 95% 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. (See Zubay, Biochemistry, Addison-Wesley Pub. Co., (1983)). It is a well-established principle of protein and peptide chemistry that certain amino acids substitutions, entitled "conservative" amino acid substitutions, can frequently be made in a protein or a peptide without altering either the conformation or the function of the protein or peptide. Such changes include substituting any of alanine (A), isoleucine (I), valine (V), and leucine (L) for any other of these amino acids; aspartic acid (D) for glutamic acid (E) and vice versa; glutamine (Q) for asparagine (N) and vice versa; serine (S) for threonine (T) and vice versa; and arginine (R) for lysine (K) and vice versa.

In addition to the known functional variants, there are derivatives of the peptides disclosed herein which can also function in the disclosed methods and compositions. Protein and peptide variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about from 2 to 6 residues are deleted at any one site within the protein or peptide molecule. These variants can be prepared by site-specific mutagenesis of nucleotides in the DNA encoding the protein or peptide, thereby producing DNA encoding the variant, and thereafter expressing the DNA in recombinant cell culture, or via solid state peptide synthesis.

Substitutional variants are those in which at least one residue has been removed and a different residue inserted in its place. Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. Similarly, the term "conformational homology" may be used herein to define a sequence which maintains a similar arrangement of amino acids from a conformational perspective to SEQ ID NO:1 or SEQ ID NO:2.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —CH$_2$NH—, —CH$_2$S—, —CH$_2$-CH$_2$-, —CH=CH-(cis and trans), —COCH$_2$-, —CH(OH)CH$_2$-, and —CHH$_2$SO-(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$-); Spatola et al. Life Sci 38:1243-1249 (1986) (—CH H$_2$-S); Hann J. Chem. Soc Perkin Trans. I 307-314 (1982) (—CH—CH—, cis and trans); Almquist et al. J. Med. Chem. 23:1392-1398 (1980) (—COCH.sub.2-); Jennins-White et al. Tetrahedron Lett 23:2533 (1982) (—COCH.sub.2-); Szelke et al. European Appln, EP 45665 CA (1982): 97:39405 (1982) (—CH(OH)CH.sub.2-); Holladay et al. Tetrahedron. Lett 24:4401-4404 (1983) (C(OH) CH.sub.2-); and HrubyLife Sci 31:189-199 (1982) (—CH.sub.2-S—); each of which is incorporated herein by reference. A particularly preferred non-peptide linkage is —CH.sub.2NH—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO: 1 or SEQ ID NO: 2, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides which contain a homing peptide fused to a second peptide having a separate function. Such bifunctional peptides have at least two functions conferred by different portions of the full-length molecule and can, for example, display anti-angiogenic activity or pro-apoptotic activity in addition to selective homing activity.

Also disclosed are isolated multivalent peptides that include at least two subsequences each independently containing a homing molecule (for example, the amino acid sequence SEQ ID NO: 1 or 2, or a conservative variant or peptidomimetic thereof). The multivalent peptide can have, for example, at least three, at least five or at least ten of such subsequences each independently containing a homing molecule (for example, the amino acid sequence of SEQ ID NO: 1 or 2, or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NO: 1 or 2, or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be affected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), .beta.,.beta.-pentamethylene cysteine (Pmc), .beta.,.beta.-pentamethylene-.beta.-mercaptopropionic acid (Pmp) and functional equivalents thereof.

Throughout this application, various publications are referenced. The disclosures of these publications in their entireties are hereby incorporated by reference into this application in order to or more fully describe the state of the art to which this pertains. The references disclosed are also individually and specifically incorporated by reference herein for the material contained in them that is discussed in the sentence in which the reference is relied upon.

It is understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed herein are peptides that enable intracellular delivery, exit and tissue penetration of compositions. The delivery can be targeted to cells or tissues of interest, such as tumors, regenerating tissue, sites of injury, surgical sites, tumor vasculature, sites of tumor angiogenesis, sites of inflammation, sites of arthritis, lung tissue, PAH lung vasculature, PAH lesions, remodeled pulmonary arteries, and interstitial space of lungs. Internalization of compositions (including nanoparticles, drugs, detectable markers, and other compounds) and their payload into target cells and penetration into target tissue can increase the efficiency of the targeting and the effectiveness of the payload.

Described herein is a peptide identified as CARSKNKDC (CAR, SEQ ID NO: 1). Also described herein is a truncated form of CAR (CARSKNK; tCAR; SEQ ID NO: 2). It was discovered that the truncated peptide is more potent for cell internalization and tissue penetration than the parent peptide CAR. These properties make tCAR a useful tool for targeted delivery of therapeutic and diagnostic agents to breast cancers and perhaps other types of tumors as well.

The disclosed tCAR peptides can be specific for a particular pathological lesion or an individual tissue. Examples include tumors, wounded tissue, diseased lung tissue, and fibrotic tissue. The ability of compositions to penetrate into the extravascular space is a major factor limiting the targeting efficacy of compositions in vivo. It has been discovered that a truncated form of the CAR homing peptide mediates highly efficient internalization of phage and free peptides into cells.

It has also been discovered that tCAR peptides specifically increase the penetration of drugs into tumors, wounded or injured tissue, regenerating tissue, injured, diseased, or fibrotic lung tissue, and other cells and tissues. Disclosed are homing peptides that specifically increase the penetration of compounds and compositions into vasculatures, tissues, and cells targeted by tCAR peptides. These peptides specifically home to target tissues, penetrate tissue, and internalize into cells. Payloads attached to these peptides, including drug, fluorophore, nanoparticle, and the like, accumulate in targeted tissues and penetrate deep into the extravascular tissues, such as extravascular tumor tissues. However, it has also been discovered that the payload does not need to be coupled to or associated with the tCAR peptide. The free tCAR peptide specifically induces tissue permeability in the targeted tissues, allowing a co-injected drug, nanoparticle, and the like, to extravasate and penetrate into the targeted tissue. This same effect can be achieved with any cells and tissue suitable for tCAR internalization.

The disclosed enhancement of internalization and tissue penetration has broad application. Using the disclosed methods, the effective targeting, delivery, and penetration of any drug, compound or composition can be augmented and enhanced. The effect of the disclosed methods has several significant implications. First, drugs and other compounds and compositions can be delivered to cells and tissues of interest at higher concentrations than is possible in standard therapy. This is a result of the increased internalization and tissue penetration mediated by the disclosed peptides. This is particularly significant because the amount of drug that can be administered is generally limited by side effects. Increasing the drug concentration at the target without increasing the amount of drug administered can thus extend and enhance the effectiveness of any known or future drugs and therapeutics. When using the disclosed methods, the increase in drug concentration only occurs in target cells and tissues and not in non-target tissues. In such cases, the efficacy of the treatment can be increased, while side effects can remain the same. Second, the dose or amount of drug or other compound or composition can be reduced without compromising the efficacy of the treatment. The disclosed methods would result in the same drug concentration at the target cell or tissue even though the amount of drug administered is less. Third, because the adjuvant peptide and the drug, imaging agent, or other compound or composition need not be coupled to one another, a validated and approved peptide can be used to augment any drug, imaging agent, or other compound or composition.

It is understood that one way to define the variants and derivatives of the disclosed proteins herein is through defining the variants and derivatives in terms of homology/identity to specific known sequences. For example, SEQ ID NO: 2 sets forth a particular sequence of tCAR. Specifically disclosed are variants of these and other peptides herein disclosed which have at least, 70% or 75% or 80% or 85% or 90% or 95% homology to the stated sequence. Wherein a sequence is said to have at least about 70% sequence identity, it is understood to also have at least about 75%, 80%, 85%, 90%, 91%, 92%, 93%, 94%, 95%, 96%, 97%, 98%, 99%, or 100% sequence identity.

It is also understood that variants and derivatives of the disclosed proteins herein may be defined by defining the variants and derivatives in terms of binding affinity to specific known sequences. For example, IdoA2S-GlcNS is a heparin sulfate moiety that when bound by CAR triggers macropinocytosis. Specifically disclosed are variants of CAR which have at least 60% or greater binding affinity to IdoA2S-GlcNS. Wherein a CAR variant is said to have at least about 60% binding affinity, it is understood to also have about 50%, 60%, 70%, 80%, 90%, 91%, 92%, 93%, 94%, 95%, 96%, 97%, 98%, 99%, or 100% binding affinity.

Previously, cell-surface heparan sulfate (HS) has been shown to be necessary for both CAR binding and internalization. When treated with heparinase I, binding of CAR to Chinese hamster ovary cells was greatly reduced. This suggested CAR's specific binding and internalization is mediated by the presence of HS moieties at the surface of the target cell. However the specific HS moiety to which CAR was binding was not specifically identified by this experiment.

In order to identify CAR's receptor additional information was required. Since previous studies have described CAR homing to pulmonary hypertensive arteries, it was deduced that the receptor for CAR must be present in PAH. It was further deduced that important clues to CAR's receptor could be found in PAH gene expression data.

In a surgical shunt model of PAH, elevated gene expression levels of HPSE, a substrate specific enzyme were found. HPSE is responsible for the cleavage of specific HS moieties (Peterson 2010). Since high levels of HPSE were found in PAH, but CAR bound strongly in PAH, we can conclude HPSE does not inhibit CAR binding and furthermore, the specific HS receptor to which CAR binds is not cleaved by HPSE. However, since heparinase I reduced CAR binding, CAR's HS receptor is cleaved by heparinase I.

Interestingly, heparinase I, the enzyme found to inhibit CAR binding, and HPSE do not have the same HS substrate specificity, and one HS moiety in particular, IdoA2S-GlcNS, is cleaved by heparinase I (Wei 2005) but not HPSE. Our PAH gene expression data also revealed extremely elevated levels of the heparan sulfate 2-O-sulfotransferase 1 (HS2ST1) gene, which encodes the HS2ST1 enzyme and is necessary for synthesis of the IdoA2S-GlcNS HS moiety, further suggesting that IdoA2S-GlcNS is present at elevated levels in PAH and is likely the CAR receptor.

Since high levels of HPSE were found in PAH, it is likely that CAR would also be useful for treating other diseases characterized by high levels of HPSE such as tumors, chronic inflammatory diseases, atherosclerosis, coronary artery disease, colitis, inflammatory bowel disorders, diabetes, arterial thrombosis, stent thrombosis, glomerular diseases, wound healing, and endometrial disorders. CAR has already demonstrated its utility in wound healing and homing properties to tumors further suggesting that CAR would be useful for treating other diseases characterized by elevated HPSE levels.

One possible mechanism by which CAR could facilitate the selective uptake of co-administered drugs is through heparan sulfate-mediated macropinocytosis. Macropinocytosis is a form of endocytosis that allows for the regulated internalization of extracellular solute molecules (Lim 2011). Studies have described the role of heparan sulfate as the receptor for lipid raft-dependent macropinocytotic internalization, and macropinocytosis has also been shown to underlie the internalization of other cationic cell-penetrating peptides (Fan 2007). Heparan sulfate mediated macropinocytosis could explain CAR's ability to increase the localized concentration of co-administered drugs without requiring the drugs to be conjugated to CAR as well as CAR's ability to promote wound healing.

Heparan sulfate-mediated macropinocytosis is a non-clathrin, non-caveolin, lipid raft-dependent form of endocytosis that allows for the regulated internalization of extracellular solute molecules (Lim 2011). HS-mediated macropinocytosis is utilized by various cationic cell-penetrating peptides (Fan 2007), and is a plausible mechanism of action to explain both CAR's ability to accelerate wound healing as well as CAR's ability to increase the localized concentration of co-administered drugs in diseased tissues. Wound healing could be accelerated through CAR administration by the selective binding of CAR to the wounded area, triggering enhanced macropinocytosis in the wounded tissues. This accelerated macropinocytosis would lead to an increased uptake of molecules involved in the body's wound healing response such as cytokines and growth factors. Similarly, the pulmonary selective vasodilation observed in animal models of PAH when CAR is co-administered with vasodilators could also be explained by this mechanism of action. CAR administration and selective binding to the area of disease would enhance HS-mediated macropinocytosis, resulting in increased localized uptake of vasodilatory drugs in the diseased pulmonary arteries and selective dilation of pulmonary vasculature.

CAR could also facilitate the selective treatment of other diseases in which CAR displays homing activity alone or in combination with other therapies by selectively increasing macropinocytosis in diseased tissues characterized by elevated levels of HPSE.

Diabetes, for example, is marked by elevated levels of HPSE (Shafat 2011, Katz 2002, Ziolkowski 2012), and the HS moiety to which CAR binds should also be present in insulin-resistant tissues in diabetes. In this case, CAR should preferentially home to inflamed, insulin-resistant tissue damaged by diabetes, and induce HS-mediated macropinocytosis upon binding specifically to the diseased tissue. This will lead to increased glucose uptake and/or improved localized performance of insulin or other diabetes medications at the site of inflammation and insulin resistance. Interestingly, reduced macropinocytosis is a hallmark of macrophages from diabetic animal models (Guest 2008). Selectively increasing macropinocytosis in inflamed tissues associated with diabetes would be an additional benefit of CAR administration in diabetes.

Further evidence of the plausibility of macropinocytosis as the mechanism of action for CAR is found in a recent experiment combining CAR with gene therapy. Based on the demonstrated success of CAR peptide as a disease-selective adjuvant that can be used with various co-administered therapeutic agents, we further sought to assess CAR's homing potential in gene therapy (GTx). Previous efforts to increase the selectivity and delivery of gene therapy vectors using cell penetrating peptides have required that the peptide be covalently or electrostatically bound to the gene therapy vector (Yao 2012). But this approach has often resulted in suboptimal results.

The MFN2 gene encodes the mitofusion-2 protein, which is a mitochondrial membrane protein that participates in mitochondrial fusion. Mitofusion-2 contributes to the maintenance and operation of the mitochondrial network, and is involved in the regulation of vascular smooth muscle cell (VSMC) proliferation. MFN2 expression is down-regulated in vascular proliferative disorders such as cancer and pulmonary hypertension, and MFN2 overexpression can attenuate the proliferation of VSMCs. Successful delivery and uptake of the MFN2 gene via adenovirus delivery vector into diseased cells results in increased expression of the mitofusion-2 protein, regulation of VSMC proliferation, and a subsequent decrease in disease indicators. We hypothesized that CAR peptide could improve the disease-selective targeting and localization of adenoviruses containing the MFN2 gene. Better localization and targeting of MFN2 gene therapy should result in increased MFN2 mRNA levels, improved mitochondrial function, and a reduction in pulmonary arterial pressure.

When we compare the results of the gene therapy experiment with the co-administration effect we see that CAR increased selective vasodilation approximately 2×, and co-administered drug concentration 2×, but gene therapy transfected gene expression increased 7×. One possible reason why gene therapy was selectively enhanced 7× while drug selectivity was only enhanced 2× is the mechanism of action by which adenoviruses transfect cells through the same lipid raft dependent macropinocytosis mechanism we are proposing for CAR's internalization. Since CAR stimulates macropinocytosis in the target tissues, the localized effects of gene therapy transfection are more enhanced by the co-administration of CAR than drug co-administration in which CAR stimulates macropinocytosis in the target tissues to increase localized drug levels. The increased enhancement of gene therapy versus drug co-administration further supports lipid raft dependent macropinocytosis as CAR's mechanism for cell penetration.

Taken together, these data identify a specific HS moiety (IdoA2S-GlcNS) as a possible receptor for CAR that could be present in pulmonary hypertensive tissues in which many of the HS moieties have been cleaved by HPSE, which is over-expressed in PAH. We further hypothesize that heparan sulfate-mediated macropinocytosis could be a plausible mechanism by which CAR binding could trigger the internalization of co-administered compounds and as a result serve as a selective enhancer of gene therapy and other therapies that utilize macropinocytosis as their route of cellular entry. CAR's selective triggering of macropinocytosis in diseased tissues by itself could also have therapeutic utility.

In one embodiment, the present invention discloses a peptide that targets the receptor IdoA2s-GlcNS and selectively penetrates the cells and extracellular matrix of diseased tissues. In a preferred embodiment the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, Crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis. In another preferred embodiment, the peptide is CAR. In another preferred embodiment, the peptide is tCAR. In yet another preferred embodiment, the peptide is a variant of CAR with at least 60% binding affinity to IdoA2s-GlcNS.

In one embodiment, the present invention discloses a method of treating a disease comprising increasing macropinocytosis. In a preferred embodiment, the increase in macropinocytosis is triggered by the presence of elevated levels of IdoA2s-GlcNS. In another preferred embodiment, the increase in macropinocytosis is triggered by the presence of elevated levels of heparinase I. In another preferred embodiment, the increase in macropinocytosis is triggered by the presence of elevated levels of HSPE. In another preferred embodiment, the increase in macropinocytosis is triggered by elevated levels of HS2ST1. In another preferred embodiment the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, Crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis.

In one embodiment, the present invention discloses a method of treating a disease comprising increasing macropinocytosis by administering to a patient suffering from a disease a therapeutically effective amount of a cell penetrating peptide. In a preferred embodiment, the peptide is CAR. In another preferred embodiment, the peptide is tCAR. In yet another preferred embodiment, the peptide is a variant of CAR with at least 60% binding affinity to IdoA2s-GlcNS. In still another preferred embodiment the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis, scleroderma, polymyositis, and dermatomyositis.

In one embodiment, the present invention discloses a method of treating a disease characterized by elevated levels of HPSE, the method comprising 1) administering a therapeutically effective amount of a compound that binds to IdoA2s-GlcNS; 2) enhancing macropinocytosis in the target tissue. In a preferred embodiment, the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis. In another preferred embodiment, the compound that binds to IdoA2s-GlcNS is CAR. In another preferred embodiment, the compound that binds to IdoA2s-GlcNS is tCAR. In yet another preferred embodiment, the compound that binds to IdoA2s-GlcNS is a variant of CAR with at least 60% binding affinity to IdoA2s-GlcNS.

In one embodiment, the present invention discloses a method of treating a disease by inhibiting macropinocystosis by administering a therapeutically effective amount of an irreversible inhibitor of IdoA2s-GlcNS. In a preferred embodiment, the inhibitor is rationally designed using current techniques when the target is known. (http://en.wikipedia.org/wiki/Drug_design) In a preferred embodiment, the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis.

In one embodiment, the present invention discloses a method of treating a disease characterized by elevated levels of HS2ST1, the method comprising 1) administering a therapeutically effective amount of a compound that binds to IdoA2s-GlcNS; 2) enhancing macropinocytosis in the target tissue. In a preferred embodiment, the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis. In another preferred embodiment, the compound that binds to IdoA2s-GlcNS is CAR. In another preferred embodiment, the compound that binds to IdoA2s-GlcNS is tCAR. In yet another preferred embodiment, the compound that binds to IdoA2s-GlcNS is a variant of CAR with at least 60% binding affinity to IdoA2s-GlcNS.

In one embodiment, the present invention discloses a method of treating a disease characterized by reduction in macropinocytosis, the method comprising 1) administering a therapeutically effective amount of a compound that binds to IdoA2s-GlcNS; 2) enhancing macropinocytosis in the target tissue. In a preferred embodiment the disease is selected from the group consisting of pulmonary hypertension, interstitial lung disease, acute lung injury (ALI), acute respiratory distress syndrome (ARDS), sepsis, septic shock, sarcoidosis of the lung, diabetes, ankylosing spondylitis, psoriasis, diseases of the endometrium, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, erectile dysfunction, chronic kidney disease, wound healing, infections, trauma injuries and systemic connective tissue diseases including systemic lupus erythematosus, rheumatoid arthritis, psoriatic arthritis, juvenile idiopathic arthritis scleroderma, polymyositis, and dermatomyositis. In another preferred embodiment, the substance administered is a peptide. In another preferred embodiment, the peptide is CAR. In another preferred embodiment, the peptide is tCAR. In another preferred embodiment, the peptide is a CAR variant with at least 60% binding affinity to IdoA2s-GlcNS. In yet another preferred embodiment, the disease is further characterized by elevated levels of one or more of HPSE, heparinase I and HS2ST1.

In one embodiment, the present invention discloses a method of treating a disease characterized by elevated levels of HPSE and heparinase I comprising the administration of a therapeutically effective amount of a composition consisting of:

1) at least one peptide selected from the group consisting of CAR, tCAR or a CAR variant with at least 60% binding affinity to IdoA2s-GlcNS; and 2) at least one other therapeutic agent.

In a preferred embodiment, the therapeutic agent is selected from the group consisting of small molecules, polypeptides, peptides, peptidomimetics, nucleic acid-molecules, cells and viruses and the like.

In one embodiment, the present invention discloses a method of treating a disease comprising increasing the localized efficacy of gene therapy by co-administering a therapeutically effective amount of a cell penetrating peptide and a gene therapy vector.

In a preferred embodiment, the peptide is CAR. In another preferred embodiment, the peptide is tCAR. In another preferred embodiment, the peptide is a variant of CAR with at least 60% binding affinity to IdoA2s-GlcNS.

In one embodiment, the present invention discloses an apparatus for determining elevated levels of disease markers wherein the disease markers are selected from the group consisting of HPSE, heparinase I, and HS2ST1. In a preferred embodiment, the apparatus further comprises imaging agents which bind to the disease markers such that the imaging agents convey the presence and/or level of the disease marker in the sample.

EXAMPLES

Recent experiments (Urakami et al. 2011; Toba et al. (in submission)) have demonstrated the ability of the pulmonary hypertensive homing, cell-penetrating peptide CAR-SKNKDC (CAR) (FIG. 2) to enhance the effects of co-administered vasodilators (fasudil, Y-27632, imatimib, and sildenafil) in selectively lowering pulmonary pressure in animal models of pulmonary arterial hypertension (PAH). Here we provide a hypothesis for CAR's mechanism of action and identify a putative receptor.

Methods

We examined data on enzymatic specificity from the literature and combined it with genetic expression in a porcine model of pulmonary hypertension to arrive at a likely target for CAR. In previous experiments, cell-surface heparan sulfate (HS) was shown to be necessary for both CAR binding and internalization (Järvinen et al. 2007). When treated with heparinase I and III, binding of CAR to Chinese hamster ovary cells was greatly reduced. This suggested that CAR's specific binding and internalization is mediated by the presence of HS moieties on the surface of the target cell.

20-30 kg Yucatan Micropigs underwent surgical anastomosis of the left pulmonary artery to the descending aorta, resulting in pulmonary arterial hypertension (Rothman et al. 2011). Endovascular samples were obtained from 2-3 mm arteries with an endoarterial biopsy catheter at baseline (prior to surgery), and from the hypertensive left lung 7, 21, 60 and 180 days after surgery. RNA was isolated from biopsy samples and loaded into an Affymetrix GeneChip Porcine Whole Genome Array containing 20, 201 *Sus scrofa* genes. Gene expression level differences were analyzed using GeneSpring, and gene expression fold changes relative to baseline were calculated (Rothman et al. 2013).

Results/Hypothesis

In a surgical shunt model of PAH, we found elevated gene expression levels of heparanase, a substrate specific enzyme responsible for the cleavage of specific HS moieties (Table 1). Interestingly, heparinase I and heparanase do not have the same HS substrate specificity, and one HS moiety in particular, IdoA2S-GlcNS, is cleaved by heparinase I but not heparanase (Table 2). Our PAH gene expression data also revealed markedly elevated levels of the heparan sulfate 2-O-sulfotransferase 1 (HS2ST1) and heparan sulfate 6-O-sulfotransferase 3 (HS6ST2) genes, which encode the HS2ST1 and HS6ST3 enzymes and are necessary for synthesis of the HS moieties resistant to heparanase (Table 1).

TABLE 1

PAH Gene Expression Data

| Gene Symbol | Name | Fold Change Day 7/Base | Fold Change Day 21/Base | Fold Change Day 60/Base | Fold Change Day 180/Base |
|---|---|---|---|---|---|
| HPSE | Heparanase | 1.59 | 13.24 | 12.75 | 2.84 |
| HS2ST1 | Heparan sulfate 2-O-sulfotransferase 1 | 22.40 | 93.98 | 26.63 | 140.44 |
| HS6ST3 | Heparan sulfate 6-O-sulfotransferase 3 | 1.12 | 21.53 | 6.33 | 2.70 |

Heparanase expression was shown to be upregulated in our PAH gene expression data. Since CAR has demonstrated selective homing in multiple models of PAH and it is known that CAR binding and internalization requires heparan sulfate receptors on target cell surfaces, CAR is most likely binding to a HS moiety that is resistant to heparanase. In a recent study, three HS moieties were shown to be resistant to heparanase (Peterson et al. 2010), but only one of the three is cleaved by heparinase I (Wei et al. 2005), an enzyme which blocks CAR internalization (Järvinen et al. 2007). Based on this enzyme specificity, we identify IdoA2S-GlcNS as a putative HS moiety to which CAR binds.

TABLE 2

Comparison of heparan sulfate substrate specificity

| Heparan sulfate moiety (below) | Heparinase I cleavage (EC 4.2.2.7) | Heparanase cleavage (EC 3.2.1.166) |
|---|---|---|
| GlcA-GlcNAc6S | No | No |
| GlcA-GlcNS | No | No |
| IdoA2S-GlcNS | Yes | No |

One possible mechanism by which CAR could facilitate the selective uptake of co-administered drugs is through heparan sulfate-mediated macropinocytosis (FIG. 5). Macropinocytosis is a non-clathrin, non-caveolin, lipid raft-dependent form of endocytosis that allows for the regulated internalization of extracellular solute molecules. Studies have described the role of heparan sulfate as the receptor for lipid raft-dependent macropinocytotic internalization (Fan et al. 2007), and macropinocytosis has also been shown to underly the internalization of other cationic cell-penetrating peptides (Lim et al. 2011; Kaplan et al. 2005; Nakase et al. 2004). Heparan sulfate mediated macropinocytosis could explain CAR's ability to increase the localized concentration of co-administered drugs without requiring the drugs to be conjugated to CAR.

Detailed description of CAR peptide binding and internalization mechanism of action is shown in FIG. 3. Specifically, healthy glycocalyx located on endothelial cell surface facing bloodstream are shown (FIG. 3a). Due to the full, in-tack glycocalyx layer, CAR cannot access its unique heparan sulfate receptors. Despite some drug molecules passively diffusing through the plasma membrane, the majority of drug will not be internalized into the healthy cell. Upon PAH injury, heparanase expression levels increase, resulting in selective enzymatic cleavage of some heparan sulfate chains and modification of the glycocalyx (FIG. 3b). HS variants resistant to heparanase cleavage remain in-tact and accessible to CAR, allowing CAR to bind to its HS receptors. Next is the initiation of heparan sulfate-mediated macropinocytosis (FIG. 3c). Binding of CAR to its HS receptors trigger lipid raft formation and membrane ruffling, causing an inward folding of the plasma membrane and engulfment of surrounding extracellular components (like CAR and drug molecules). Vesicles (called macropinosomes) containing CAR and drug molecules are formed and internalized into the cell (FIG. 3d). Finally, the reduced intracellular pH causes the macropinosome to dissociate, releasing its contents (CAR and drug) into the diseased cell (FIG. 3e).

Conclusions

These data identify a specific HS moiety (IdoA2S-GlcNS) as a possible receptor for CAR that could be present in pulmonary hypertensive tissues, in which most other HS moieties have been cleaved by high levels of heparanase. We further hypothesize that heparan sulfate-mediated macropinocytosis could be a plausible mechanism by which CAR binding could promote the internalization of co-administered compounds. Experiments are currently underway to test and refine these hypotheses, while CAR is being developed as a therapeutic adjuvant for PAH.

Abbreviations

CAR—a 9 amino acid cyclic peptide CARSKNKDC (where the amino acids C=cysteine, A=alanine, R=arginine, S=serine, K=lysine, N=asparagine, D=aspartic acid)

TAT—trans-activator of transcription protein

PAH—pulmonary arterial hypertension

GTx—gene therapy

EC—enzyme classification

HIV—human immunodeficiency virus

MFN2—mitofuson-2 gene

HPSE—heparanase

HS—heparan sulfate

HS2ST1—heparan sulfate 2-O-sulfotransferase 1 gene

RNA—ribonucleic acid mPAP—mean pulmonary arterial pressure mmHG—millimeters of mercury cDNA—complementary deoxyribonucleic add (DNA)

MFN2-CAR—mitofusion-2 gene therapy combined with CAR peptide (co-administration)

VSMC—vascular smooth muscle cells tCAR—truncated CAR (CARSKNK)

CAR variants (take from previous patent apps)

RV/LV-S—right ventricle to left ventricle plus septum (weight ratio of)

Sugen Hypoxia Rats—rats that are given sugen (a vascular endothelial growth factor [VEGF] Inhibitor), then placed in a hypoxia (10% oxygen) chamber CH-SU Rats—chronic hypoxia-sugen rats SMP—selective macropinocytosis promoter References:

Frankel A D, Pabo, C O. Cellular uptake of the tat protein from human immunodeficiency virus. *Cell.* 1988; 55:1189-1193.

Green M, and Loewenstein P M. Autonomous functional domains of chemically synthesized human immunodeficiency virus tat trans-activator protein. *Cell.* 1988; 55:1179-1188.

Lindsay M A. Peptide-mediated cell delivery: application in protein target validation. *Curr Opin Pharmacol.* 2002; 2:587-594.

Wadia J S, Dowdy S F. Modulation of cellular function by TAT mediated transduction of full length proteins, *Curr Protein Pept Sci.* 2003; 4:97-104.

Snyder E, Dowdy S F. Cell penetrating peptides in drug delivery. *Pharm Res.* 2004; 21:389-393.

Säälik P, Elmquist A, Hansen M, Padari K, Saar K, Viht K, Langel U, Pooga M. Protein cargo delivery properties of cell-penetrating peptides. A comparative study. *Bioconjug Chem.* 2004; 15:1246-53.

Johnson R M, Harrison S D, Maclean D, Langel U. Therapeutic Applications of Cell-Penetrating Peptides. *Methods in Molecular Biology.* Vol 683.

Nishimura S, Takahashi S, Kamikatahira H, Kuroki Y, Jaalouk D E, O'Brien S, Koivunen E, Arap W, Pasqualini R, Nakayama H, and Kuniyasu A. Combinatorial Targeting of the Macropinocytotic Pathway in Leukemia and Lymphoma Cells. *J Bio Chem.* 2008; 283:11752-11762.

Kaplan I M, Wadia J S, Dowdy S F. Cationic TAT peptide transduction domain enters cells by macropinocytosis. *Journal of Controlled Release.* 2005; 102:247-253.

Niesner U, Halin C, Lozzi L, Ounthert M, Neri P, Wunderli-Allenspach H, Zardi L, Neri D. Quantitation of the tumor-targeting properties of antibody fragments conjugated to cell-permeating HIV-1 TAT peptides. *Bioconjugate Chem.* 2002; 13:729-736.

Guest C B, Chakour K S, Freund G G. Macropinocytosis is decreased in diabetic mouse macrophages and is regulated by AMPK. *BMC Immunology.* 2008; 9:42.

Peterson S B, Liu J. Unraveling the specificity of heparanase utilizing synthetic substrates. Journal of Biological Chemistry. 2010; 285:14504-13.

Brooks H, Lebleu B, Vives E. Tat peptide-mediated cellular delivery: back to basics. Advanced Drug Delivery Reviews. 2005; 57:559-577.

Fan T C, Chang H T, Chen I W, Wang H Y, Chang M D T. A heparan sulfate-facilitated and raft-dependent macropinocytosis of eosinophil cationic protein. Traffic. 2007; 8:1778-1795.

Lim J P, Gleeson P A. Macropinocytosis: an endocytic pathway for internalising large gulps. Immunology and Cell Biology. 2011; 89:836-843.

Shafat I, Ilan N, Zoabi S, Vlodavsky I, Nakhoul F. Heparanase levels are elevated in the urine and plasma of type 2 diabetes patients and associate with blood glucose levels. PLoS ONE. 2011; 6:17312.

Wei Z, Lyon M, Gallagher J T. Distinct substrate specificities of bacterial heparinases against N-unsubstituted glucosamine residues in heparan sulfate. Journal of Biol Chem. 2005; 280:15742-15748.

Yao X L, Yoshioka Y, Ruan G X, Chen Y Z, Mizuguchi H, Mukai Y, Okada N, Gao J Q, Nakagawa S. Optimization and internalization mechanisms of PEGylated adenovirus vector with targeting peptide for cancer gene therapy. Biomacromolecules. 2012 Aug. 13; 13(8):2402-9. Epub 2012 Jul. 23.

Ruoslahti E., Rajotte D. An address system in the vasculature of normal tissues and tumors. Annu. Rev. Immunol. 2000; 18:813-27.

Katz A, Van-Dijk D J, Aingorn H, Erman A, Davies M, Darmon D, Hurvitz H, Vlodavsky I. Involvement of human heparanase in the pathogenesis of diabetic nephropathy. Isr Mod Assoc J. 2002 November; 4(11):996-1002.

Ziolkowski A F, Popp S K, Freeman C, Parish C R, Simeonovic C J. Heparan sulfate and heparanase play key roles in mouse β cell survival and autoimmune diabetes. J Clin Invest. 2012 January 3; 122(1):132-41. doi: 10.1172/JCI46177. Epub 2011 Dec. 19.

Urakami T, Järvinen T A H, Oka M, Sawada J, Ambalavanan N, Mann D, McMurtry I, Ruoslahti E, Komatsu M. Peptide-directed highly selective targeting of pulmonary arterial hypertension. Am J Pathol 2011; 178:2489-2495.

Toba M, Alzoubi A, O'Neill K, Abe K, Urakami T, Komatsu M, Alvarez D, Järvinen T A H, Mann D, Ruoslahti E, McMurtry I F, Oka M. The tissue-penetrating homing peptide CAR selectively enhances pulmonary effects of systemically co-administered vasodilators in a preclinical model of severe PAH. (In submission).

Järvinen T A, Ruoslahti E. Molecular changes in the vasculature of injured tissues. *The American journal of pathology* 2007; 171:702-711.

Nakase I, Niwa M, Takeuchi T, Sonomura K, Kawabata N, Koike Y, Takchashi M, Tanaka S, Ueda K, Simpson J C, Jones A T, Sugiura Y, Futaki S. Cellular uptake of arginine-rich peptides: roles for macropinocytosis and actin rearrangement. *Molecular Therapy* 2004; 10:1011-1022.

Rothman A, Wiencek R G, Davidson S, Evans W, Restrepo H, Sarukhanov V, Rivera-Begeman A, Mann D. Hemodynamic and histologic characterization of a swine (*Sus scrofa domestica*) model of chronic pulmonary arterial hypertension. *Comparative Medicine* 2011; 61(3): 258-262.

Rothman A, Davidson S, Wiencek R G, Evans W N, Restrepo H, Sarukhanov V, Ruoslahti E, Williams R, Mann D. Vascular histomolecular analysis by sequential endoarterial biopsy in a shunt model of pulmonary hypertension. *Pulm Circ.* 2013 January; 3(1):50-7.

I claim:

1. A method of increasing the concentration of co-administered drugs in an individual with a disease characterized by tissues with increased heparan sulfate moiety, the method comprising:

a) screening an individual for increased levels of a heparin sulfate moiety selected from the group consisting of 2-O-sulfo-α-L-iduronic acid-2-deoxy-2-acetamido-α-D-glucopyranosyl, IdoA2S-GlcNS, heparinase I, and heparanase (HPSE);

b) identifying the presence of a disease requiring treatment according to the increased levels of the compound detected in step a) wherein the disease is pulmonary hypertension (PAH);

c) administering to said individual a peptide that targets the receptor IdoA2S-GlcNS and selectively penetrates the cells and extracellular matrix of diseased tissues wherein the peptide is selected from the group consisting of CAR (SEQ ID NO: 1) and tCAR (SEQ ID NO: 2);

d) co-administering to said individual a drug for treatment of PAH with said peptide; and e) increasing the rate of macropinocytosis in the target cells.

2. The method of claim 1, wherein the peptide is CAR.

* * * * *

UNITED STATES PATENT AND TRADEMARK OFFICE
CERTIFICATE OF CORRECTION

PATENT NO. : 9,603,890 B2
APPLICATION NO. : 14/649455
DATED : March 28, 2017
INVENTOR(S) : Mann It is certified that error appears in the above-identified patent and that said Letters Patent is hereby corrected as shown below:

In the Specification

Column 5, Line 43: delete the "," after the word "codons";

Column 6, Line 36: delete the second occurrence of the word "in";

Column 7, Line 32: replace the ";" with a --:--;

Column 7, Line 40: delete the second occurrence of the word "in";

Column 8, Line 13: delete the "," after the word "data";

Column 9, Line 13: delete the "," after the word "as";

Column 12, Line 62: insert a --,-- after the word "enzyme";

Column 13, Line 38: insert a --,-- after the word "CAR";

Column 15, Line 33: delete the "," after the word "nodes";

Column 16, Line 8: delete the "," after the word "nodes";

Column 16, Line 45: delete the "," after the word "nodes";

Column 17, Line 11: delete the "," after the word "nodes";

Column 17, Line 32: insert a --.-- after the ")";

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,603,890 B2

Column 17, Line 51: delete the "," after the word "nodes";

Column 18, Line 17: delete the "," after the word "nodes";

Column 18, Line 56: delete the "," after the word "nodes"; and

Column 21, Line 32: the word "trigger" should read "triggers".